US006171862B1

(12) United States Patent
Abe et al.

(10) Patent No.: US 6,171,862 B1
(45) Date of Patent: Jan. 9, 2001

(54) TRANSFECTION IN SERUM-CONTAINING MEDIA

(75) Inventors: Akihiro Abe; Atsushi Miyanohara; Theodore Friedmann, all of San Diego, CA (US)

(73) Assignee: The Regents of the University of California, Oakland, CA (US)

( * ) Notice: Under 35 U.S.C. 154(b), the term of this patent shall be extended for 0 days.

(21) Appl. No.: 09/052,797

(22) Filed: Mar. 31, 1998

(51) Int. Cl.$^7$ ............................ C12N 15/87; C12N 15/88; C07H 21/04

(52) U.S. Cl. ............................ 435/455; 435/458; 530/344; 530/350

(58) Field of Search .............................. 435/69.1, 320.1, 435/455, 458; 530/350, 344

(56) References Cited

U.S. PATENT DOCUMENTS

| | | | |
|---|---|---|---|
| 5,512,421 | 4/1996 | Burns et al. | 435/320.1 |
| 5,578,475 | * 11/1996 | Jessee | 435/456 |
| 5,627,159 | * 5/1997 | Shih et al. | 514/44 |

OTHER PUBLICATIONS

Andreadis, S., and Palsson, B., 1997, "Coupled Effects of Polybrene and Calf Serum on the Efficiency of Retroviral Transduction and the Stability of Retroviral Vectors," Hum. Gen Ther. 8:285–291.

Brunette, E., et al., 1992, "Lipofection does not require the removal of serum," Nucl. Acids Res. 20:1151.

Burns, J.C., et al., 1993, "Vesicular stomatitis virus G glycoprotein pseudotyped retroviral vectors: Concentration to very high titer and efficient gene transfer into mammalian and nonmammalian cells," Proc. Natl. Acad. Sci. USA 90:8033–8037.

Chen, S.T., et al., 1996, "Generation of packaging cell lines for pseudotyped retroviral vectors of the G protein of vesicular stomatitis virus by using a modified tetracycline inducible system," Proc. Natl. Acad. Sci. USA 93:10057–10062.

Emi, N., et al., 1991, "Pseudotype Formation of Murine Leukemia Virus with the G Protein of Vesicular Stomatitis Virus," J. Virol 65:1202–1207.

Felgner, P.L. et al., 1987, "Lipofection: A highly efficient, lipid–mediated DNA–transfection procedure," Proc. Natl. Acad. Sci. USA 84:7413–17.

Felgner, P.L., et al., 1995, "Improved Cationic Lipid Formulations for In Vivo Gene Therapy," *DNA Vaccines, a New Era in Vaccinology*, Ann. NY Acad. Sci. 772:126–139.

Gao, X., and Huang, L., 1996, Biochemistry 35:1027–1036.

Hofland, E.E., et al., 1996, "Formation of stable cationic lipid/DNA complexes for gene transfer," Proc. Natl. Acad. Sci. USA 93:7305–7309.

Hong, K., et al., 1997, "Stabilization of cationic liposome–plasmid DNA complexes by polyamines and poly(ethylene glycol)–phospholipid conjugates for efficient in vivo gene delivery," FEBS Lett. 400:233–237.

Hug, P., and Sleight, R.G., 1994, "Fusogenic Virosomes Prepared by Partitioning of Vesicular Stomatitis Virus G Protein Into Preformed Vesicles," J. Biol. Chem 269:4050–4056.

Metsikko, K., et al., 1986, "Reconstitution of the fusogenic activity of fsicular stomatitis virus," EMBO J. 5:3429–3435.

Mizuguchi, H., et al., 1996, "Efficient Gene Transfer Into Mammalian Cells Using Fusogenic Liposome," Biochem. Biophys. Res. Com. 218:402–407.

Petri, W.A., and Wagner, R.R., 1979, "Reconstitution Into Liposomes of the Glycoprotein of Vesciular Stomatitis Virus by Detergent Cialysis," J. Biol. Chem. 254:4313–4316.

Sharma, S., et al., 1997, "Noninfectious virus–like particles produced by Moloney murine leukemia virus–based retrovirus packaging cells deficient in viral envelope become infectious in the presence of lipofection reagents," Proc. Natl. Acad. Sci. USA 94:10803–10808.

Singh, D., and Rigby, P.W.J., 1996, "The use of histone as a facilitator to improve the efficiency of retroviral gene transfer," Nucl. Acids Res. 24:3113–3114.

Stephan, D.J., et al., 1996, "A New Cationic Liposome DNA Complex Enhances the Efficiency of Arterial Gene Transfer In Vivo," Hum. Gene Ther. 7:1803–1812.

Yee, J.K., et al., 1994, "A general method for the generation of high–titer, pantropic retroviral vectors: Highly efficient infection of primary hepatocytes," Proc. Natl. Acad. Sci. USA 914:9564–9568.

Zabner, et al., 1995, "Cellular and Molecular Barriers to Gene Transfer by a Cationic Lipid," J. Biol. Chem. 270:18997–19007.

* cited by examiner

Primary Examiner—David Guzo
(74) Attorney, Agent, or Firm—Foley & Lardner

(57) ABSTRACT

Transfection of host cells cultured in the presence of serum is increased by adding VSV-G or polybrene to a nucleic acid-lipid complex or culture medium prior to transfection.

13 Claims, 4 Drawing Sheets

SEQUENCE LISTING (1) GENERAL INFORMATION:

(iii) NUMBER OF SEQUENCES: 1

(2) INFORMATION FOR SEQ ID NO:1:

-continued

```
    (i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

ATATCCACAA CTCTGCAGAG GGAACCCGGG ATTCAGCCA                                    39
```

TRANSFECTION IN SERUM-CONTAINING MEDIA

STATEMENT AS TO FEDERALLY SPONSORED RESEARCH

This invention was made with Government support under one or more of the following grants: Grant No. 5ROI HL 53680-3 and/or No. 5ROI DK 49023-2, awarded by the National Institutes of Health. The Government may have certain rights in this invention.

FIELD OF THE INVENTION

This invention relates to the fields of molecular biology and gene therapy, and more particularly to improved methods for transfecting cells in the presence of culture media containing serum.

BACKGROUND OF THE INVENTION

Cationic lipid-mediated gene transfer (lipofection) is a simple and efficient technique for introducing foreign genetic information into cultured mammalian cells (P. L. Feigner et al., *Proc Natl Acad Sci USA* (1987) 84:7413–17; P. L. Feigner et al., *Ann NY Acad Sci* (1995) 772:126–39). Although it is a widely used gene transfer technique, it is hampered by several disadvantages, including low gene transfer efficiency in some cell types, instability and serum-induced inactivation of the DNA-lipid complex, and cell toxicity of the lipofection procedure. In most cell lines, cationic liposome-mediated transfection requires serum depletion.

A number of approaches have been tried to overcome these disadvantages. H. E. Hofland et al., *Proc Natl Acad Sci USA* (1996) 93:7305–09, reported the formation of stable DNA-lipid complexes that retain their efficiency of gene transfer even in the presence of serum in culture medium, and that remain active for up to three months. Mizuguchi et al. reported that the fusogenic liposomes formed by cationic lipid-DNA complex and Sendai virus retained 70% of their transfection efficiency even in the presence of 40% fetal bovine serum (FBS) in contrast to the virtual inactivity of complexes formed without Sendai virus, even in the presence of as little as 5% FBS.

The polycation polybrene is used routinely to enhance the efficiency of retrovirus vector-mediated gene transfer. S. Andreadis et al., *Hum Gene Ther* (1997) 8:285–91, have recently reported that the concentrations of polybrene required for optimum retrovirus-mediated gene transfer increase with increasing concentrations of serum. X. Gao et al., *Biochemistry* (1996) 35:1027–36, have also reported that the efficiency of cationic liposome mediated gene transfer in vitro can be enhanced up to 2 to 28-fold by the use of a polycation. Adding a polycation during DNA-lipid complex formation resulted in complexes having a reduced particle size, leading to higher efficiency.

SUMMARY OF THE INVENTION

We have now invented an improved method for transfecting cells in the presence of serum. The method comprises preparing a complex of cationic lipid and nucleic acid, and adding VSV-G protein and/or polybrene to the preformed complex. Alternatively, the polybrene may be added to the culture medium just prior to adding the preformed complex. The resulting complex is capable of transfecting cells even in the presence of substantial amounts of serum.

One aspect of the invention is a method for introducing nucleic acids into a host cell in the presence of interfering serum components, by providing a nucleic acid-lipid complex and a host cell in a medium comprising an interfering component, and contacting the host cell with the nucleic acid-lipid complex and an effective amount of a transfection aid, wherein the transfection aid is either VSV-G or a polycation.

Another aspect of the invention is a method for preparing VSV-G for use as a transfection aid, by providing a producing cell comprising an expression vector encoding VSV-G operable in the producing cell, culturing the producing cell in medium under conditions which result in expression of VSV-G to provide a conditioned medium, and purifying VSV-G from the conditioned medium by centrifugation under non-denaturing conditions to provide fusogenically active VSV-G.

Another aspect of the invention is a composition for effecting lipid-mediated transfection in the presence of interfering cell culture components, said composition comprising a transfection-effective lipid, and an effective amount of a transfection aid selected from the group consisting of VSV-G and a polycation.

Another aspect of the invention is a composition for effecting lipid-mediated transfection in the presence of interfering cell culture components, said composition comprising an effective amount of non-denatured, fusogenically active VSV-G and a non-toxic carrier.

One object of the invention is to provide a method for transfecting cells by lipofection in the presence of interfering components, for example in the presence of serum-containing medium.

Another object of the invention is to provide a composition suitable as a lipofection aid, capable of overcoming the deleterious effects of serum on lipofection.

Another object of the invention is to provide a lipofection aid that is simple to prepare and use.

Another object of the invention is to provide a method for preparing VSV-G under conditions that preserve its fusogenic activity, rendering it usable as a lipofection aid.

DESCRIPTION OF THE PREFERRED EMBODIMENTS

Figure 1A:
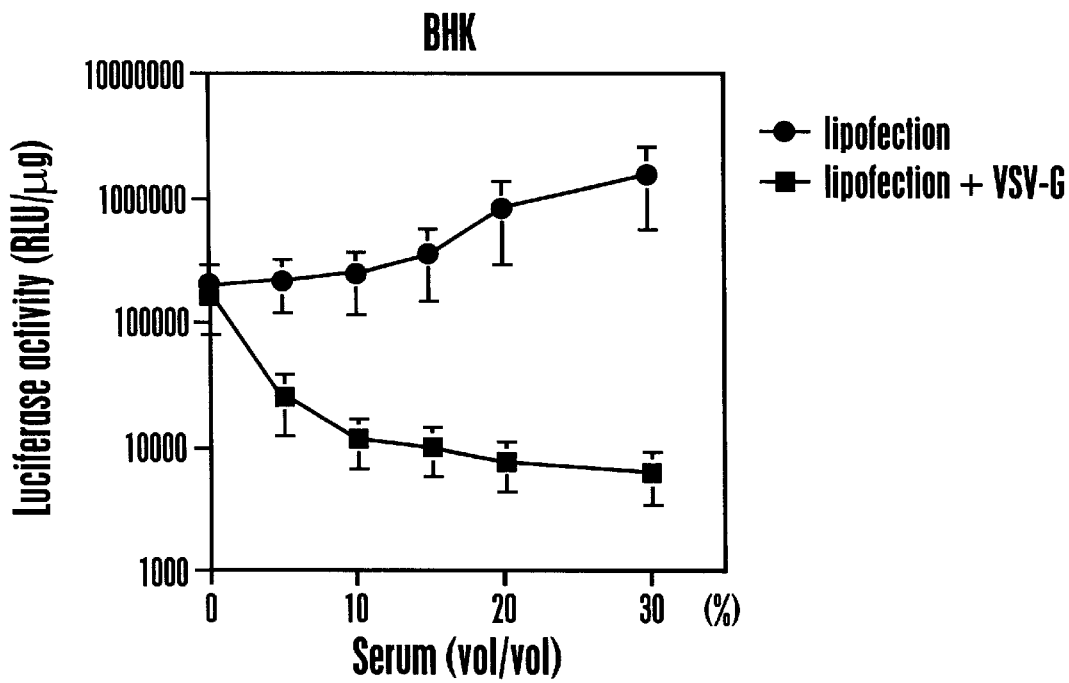
FIG. 1 shows the results of transfecting BHK cells (FIG. 1A) or 208F cells (FIG. 1B) with or without VSV-G, in the presence of varying amounts of serum.

Definitions:

The term "polybrene" as used herein refers to the compound

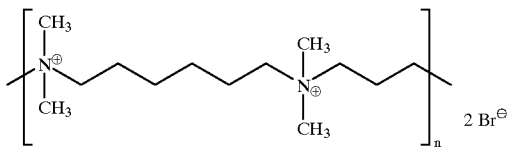

variously referred to as hexadimethrine bromide, poly(N,N, N', N'-tetramethyl-N-trimethylenehexamethylenediammonium dibromide), and Polybrene. It may be considered a copolymer of N,N,N',N'-tetramethyl-1,6-hexanediamine with 1,3-dibromopropane. Polybrene generally has a molecular weight in the range of about 5,000 to about 20,000.

The term "polycation" refers to a polymeric molecule having a plurality of positive charges distributed thereon. Suitable polycations have a molecular weight of at least 200, preferably more than 1,000, more preferably more than 5,000. Polycations preferably have a molecular weight less than about 75,000, more preferably less than about 50,000, most preferably less than about 20,000. Exemplary polycations include polyamides, protamine sulfate, and polybrene.

The term "VSV-G" as used herein refers to an isolated polypeptide having substantial homology to the G protein of vesicular stomatitis virus. A polypeptide has substantial homology to the VSV G protein if it exhibits the membrane-fusing properties of the wild-type protein to a substantial degree. One may use the full-length protein, or may delete portions, as long as the protein is still substantially able to associate with nucleic acid-lipid particles and facilitate transfection. VSV-G of the invention preferably does not include other viral proteins.

The term "transfection aid" as used herein refers to an agent which, when added to a complex of nucleic acid and transfection lipid in suitable quantities, is sufficient to overcome the deleterious effect of serum in the culture medium on transfection. Transfection aids are selected from the group consisting of VSV-G proteins and polycations such as polybrene. An effective amount of a transfection aid is that quantity which produces a measurable increase in transfection efficiency for a given host cell cultured in the presence of serum.

The term "transfection" as used herein refers to the process of introducing nucleic acids into a host cell, without the use of a virus or viral particle carrier. "Lipid transfection" as used herein refers to transfection which is mediated or facilitated using lipids or liposomes. Liposomes are small vesicles formed from bilayers of amphipathic molecules such as dipalmitoylphospatidyl ethanolamine, dioleylphosphatidyl ethanolamine, stearate salts, cholesterol, and the like. Liposomes may have a single bilayer or multiple bilayers, and may be prepared by a variety of different methods. Other lipids may be used for lipid transfection without forming liposomes, such as for example Lipofectin® (also known as DOTMA, N[1-(2,3-dioleyloxy)-propyl]-N,N,N-trimethylammonium chloride, Life Technologies, Inc.). These lipids are believed to form complexes with free nucleic acids, without necessarily adopting a liposome-like structure. Complexes of nucleic acids with either liposomes or non-liposomal lipids are referred to herein as "nucleic acid-lipid complexes."

The term "interfering component" refers to one or more constituents normally found in serum which, singly or together, act to reduce the efficiency of lipid-mediated transfection if added to the host cell culture medium. The method of the invention is useful for overcoming the reduction in efficiency due to interfering components, regardless of whether they are added as serum, individually, or in the form or other mixtures or supplements.

General Description

Transfection is the method used for introducing nucleic acids (typically foreign or heterologous nucleic acids) into a host cell. The present invention concerns introducing nucleic acids into a host cell without using a viral particle or intact virus.

The nucleic acid to be used will be dictated by the desired effect. In general, one may use the method of the invention to insert any nucleic acid, including DNA, RNA, DNA/RNA hybrids, and nucleic acids containing altered or non-natural bases or moieties. Nucleic acids are typically provided in the form of plasmids or recombinant viral vectors.

The host cells to be used are also dictated by the desired effect or experiment. However, the instant invention is designed to optimize transfection of mammalian cells, particularly cells cultured in the presence of serum. Accordingly, the method of the invention is particularly well suited for transfection of host cells that require or benefit from the presence of serum in their culture medium. Exemplary host cells include BHK cells, 293 cells, 208F cells, and the like.

In the practice of the invention, the host cells are cultured under optimum conditions for the cell type selected, in a culture medium containing a beneficial amount of serum, typically fetal bovine serum (FBS). The DNA to be inserted is combined with a lipid transfection agent, such as Lipofectin, to form a DNA-lipid complex. The complex is then combined with an effective amount of a transfection aid, preferably either VSV-G or polybrene, and added directly to the host cell culture, or a transfection aid (such as polybrene) may be added directly to the culture medium just before adding the preformed DNA-lipid complex to the cell. The transfected host cells are then cultured normally.

To prepare VSV-G for use in the method of the invention, it is sufficient to partially purify VSV-G obtained from conditioned medium by centrifugation, preferably ultracentrifugation, without the use of detergents. Centrifugation conditions are selected to pellet VSV-G without substantially denaturing the protein. For example, one may centrifuge conditioned medium (preferably from cells transfected to express VSV-G in the absence of other VSV proteins) at about 14,000 rpm to about 35,000 rpm, for example at about 24,000 rpm. The centrifugation time may range from about 30 minutes to about 150 minutes, for example about 90 minutes. The resulting pellet is resuspended in PBS. If desired, one may further purify the VSV-G by velocity sedimentation. Velocity sedimentation may be performed, for example, by using a 5%–30% sucrose gradient, centrifuging at about 30,000 for about 25 minutes and collecting the appropriate fractions.

VSV-G purified in this manner may be formulated with appropriate buffers and preservatives to provide a composition in suitable form for immediate use as a lipofection aid. If desired, the VSV-G may be formulated in combination with a lipofection agent, or packed in packaging that includes a lipofection agent. VSV-G may also be lyophilized under non-denaturing conditions to provide a dry powder suitable for reconstitution and suspension prior to use as a transfection aid.

The amount of transfection aid required for a particular cell type and/or serum concentration may be determined by transfecting the desired host cells with a marker gene (a gene which produces a detectable product following transfection) under the conditions desired, and quantifying the number of successfully transfected cells (or by quantifying the amount of marker product produced) given various concentrations of transfection aid, for example following the procedures described in the Examples below.

It is possible that the deleterious effect of serum on lipid-mediated transfection is due to one or several components normally present within serum, and that these component(s) are specifically countered by the use of a transfection aid as employed herein. Thus, it is to be expected that a synthetic culture medium, or one fortuitously supplemented with one or more of the unidentified interfering components would also demonstrate deleterious effects on lipid-mediated transfection. The method of the invention is useful for increasing the efficiency of transfection in the presence of such components, whether they are added individually or in the form of serum.

EXAMPLES

The following examples are provided as an illustration of the invention, and are not intended to limit the scope of the claimed invention in any way. Unless otherwise specified, all experiments are conducted at ambient conditions.

Example 1

Transfection Employing VSV-G

Lipofectin was obtained from GIBCO BRL/Life Technologies (Grand Island, N.Y.). Plasmids pCMV-G and pCMV-luc plasmid expressing VSV-G or firefly luciferase, respectively, from the human cytomegalovirus promoter have been previously described by Yee et al., *Proc Natl Acad Sci USA* (1994) 91:9564–68). Luciferase activity in the transfected cells was measured and its activity presented as relative light units (RLU), as described by Xu et al., *Virology* (1989) 171:331–41.

A fusion-defective mutant VSV-G ("P127L"), containing a $Pro_{127}$-Leu substitution, was prepared using the MORPH in vitro mutagenesis kit (5prime-3prime Inc., Boulder, Colo.). The mutagenesis primer 5'-ATATCCACAACTCTGCAGAGGGAACCCGGGATTC AGCCA-3' (SEQ ID NO:1) also includes a number of silent mutations. An identical mutant has previously been reported by Zhang et al., *J Virol* (1994) 68:2186–93. Although VSV-G-P127L is expressed well on cell surface, and is released efficiently into culture medium, its cell fusion function is less than 5% of wild-type VSV-G.

Plasmids were amplified in *E. coli* (DH5a) and grown in LB medium. Bacteria were lysed and plasmid purified according to established methods, using CsCl gradient ultracentrifugation. The neutralizing monoclonal antibody to VSV-G is described by Lefrancois et al., *Virology* (1982) 121:157–67.

(A) Lipofection with VSV-G: DNA-lipid complexes were prepared using Lipofectin according to the manufacturer's instructions, and were mixed with VSV-G just prior to transfection. All transfections were performed on cell cultures at approximately 80% confluency. Cells grown in 6-well or 12-well plates were washed twice with DMEM and were maintained in fresh DMEM containing various concentrations of FBS, and incubated with DNA-lipid complex. DNA-lipid complex was prepared with reduced volume as follows: for the 12-well plate, 2.5 µg of lipofectin was diluted with 50 µl of DMEM for each well. After incubation for 30 min at room temperature, the diluted lipofectin was mixed with 0.5 µg of DNA in 50 µl of DMEM and incubated for 15 min at room temperature and subjected to transfection. For 6-well plates, amounts of each compound were doubled. Culture medium was changed with fresh DMEM+10% FBS after 12 hours of incubation.

For experiments with the stable transformant, 293 cells were transfected with plasmid pcDNA3 (Invitrogen, Carlsbad, Calif.), which contains neomycin resistance gene under control of the SV40 promoter. Serially diluted cells were spread on 10 cm plates 24 hours after transfection, and G418 selection was started 48 hours after transfection. G418-resistant colonies were counted after 2 weeks of selection.

(B) VSV-G Preparation: The conditioned medium from 293 cells transfected with plasmid pCMV-G was centrifuged at 24,000 rpm (Beckman SW28 rotor) for 90 min. Ultracentrifuged pellets of VSV-G particles were resuspended in 1 ml PBS and layered on 5%–30% continuous sucrose gradients for velocity sedimentation. Solutions were prepared in PBS (pH 7.5). The gradients were centrifuged at 30,000 rpm (SW41Ti rotor) for 25 min, and fractions containing VSV-G were collected, diluted with PBS and centrifuged at 30,000 rpm for 90 min. Resulting VSV-G pellets were resuspended with PBS and the protein amount quantified with BCA protein detection kit (Pierce, Rockford, Ill.). Aliquots of VSV-G particles were reserved at −80° C. until use. The proteins were analyzed by SDS-PAGE on a 7.5% gel and visualized with silver staining kit (Bio-Rad, Richmond, Calif.).

(C) Results: Pelleted VSV-G was resuspended with PBS and protein was assayed as described above. The VSV-G pellets from transfected cells was detected as a band of approximately 68 kD in size, with significant amounts of 75 kD (possibly representing bovine serum albumin). After velocity sucrose gradient sedimentation and repelleting, the purity of the VSV-G was substantially improved, as judged by silver staining. Approximately 20–30 µg of VSV-G protein from 200 ml of conditioned 293 cell medium was routinely obtained.

As shown in Table 1, addition of VSV-G to DNA-lipid complex increased the lipofection efficiency approximately 10 fold in the presence of 10% FBS in culture medium, as estimated by luciferase activity 48 hours after transfection in both BHK cells and 293 cells, or by the number of stable, G418-resistant colonies in 293 cells 14 days after transfection. In all cases, this enhanced transfection was inhibited by anti-VSV-G neutralizing antibody I1, and was not seen with the fusion-defective VSV-G mutant, VSV-G-P127L. We therefore conclude that the enhancement of lipofection by VSV-G requires the fusogenic function of VSV-G. Neither luciferase activity nor G418 resistance was seen after exposure of the cells to DNA or VSV-G without lipofectin.

To optimize the composition of the lipofectin-DNA-VSV-G complexes during lipofection, we examined the effect of increasing amounts of VSV-G added to constant amounts (2.5 µg) of the DNA-lipid complex immediately prior to addition to cells. When 2.5 µg of DNA-LIPID was mixed with amounts of partially purified VSV-G ranging from 10 ng to 1 µg, lipofection efficiency on both BHK and 208F cells increased in a dose-dependent manner and reached a maximum efficiency at approximately 300–400 ng of VSV-G. Amounts of VSV-G greater than 400 ng slightly decreased the transfection efficiency, although the decrease was not correlated to the known toxicity of VSV-G (syncytium formation).

TABLE 1

Effect of VSV-G on Lipofection
Luciferase activity (RLU/μg)

| Transfection aid | BHK cells | 293 cells | stable transformants (colonies/ 2 × 10³ cells) |
|---|---|---|---|
| DNA-lipid | 40,900 ± 800 | 16,700 ± 700 | 8 |
| DNA-lipid + VSV-G | 442,000 ± 11,100 | 125,000 ± 5,300 | 62 |
| DNA-lipid + anti-VSV-G | 32,000 ± 700 | 13,300 ± 800 | 10 |
| DNA-lipid + VSV-G + anti-VSV-G | 26,700 ± 800 | 12,400 ± 500 | 11 |
| DNA-lipid + VSV-G-P127L | 28,300 ± 900 | 13,600 ± 700 | 12 |

Figure 1B:
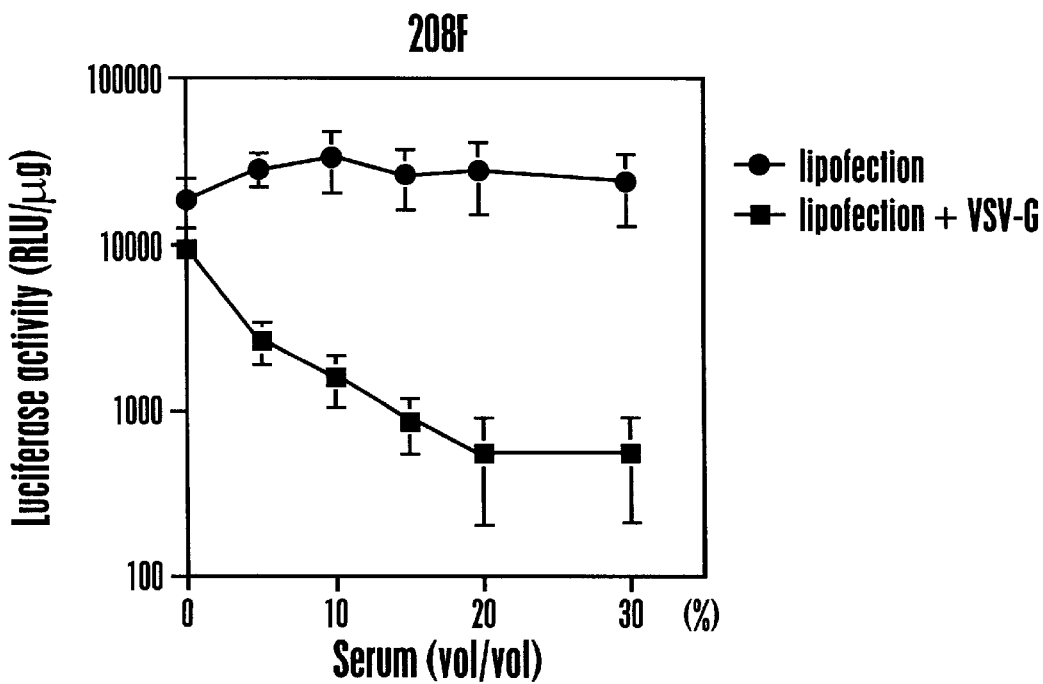

In many cell lines, maximum efficiency of lipofection is known to require serum-depleted or serum-free media, even though such conditions are in themselves toxic to many cell types. For such cell lines, it would be advantageous to have lipofection conditions that allow efficient gene transfer in the presence of serum. We therefore examined the effect of serum on lipofection in the presence of VSV-G. As shown in FIG. 1, serum-mediated inhibition of lipofection was completely abrogated. In the case of BHK cells, high concentrations of serum may even have a further moderate enhancing effect on lipofection efficiency.

To examine the mechanism of the VSV-G-mediated enhancement of lipofection, we analyzed the association of VSV-G with DNA-lipid complex by equilibrium buoyant density sucrose gradient sedimentation. Partially purified VSV-G (2.5 μg) or DNA-lipid complex (50 μg of lipid, 10 μg of pCMV-luc) or VSV-G-DNA-lipid complex (2.5 μg VSV-G, 50 μg lipofectin, 10 μg of pCMV-luc) were layered on 5%–40% continuous sucrose gradients prepared in PBS (pH 7.5). The gradients were centrifuged at 35,000 rpm (SW41Ti rotor) for 16 hours at 4° C. Fractions were collected from the top of the gradient. Transfection efficiency was measured by luciferase activity with non-serum condition as described above. VSV-G was detected by Western blotting, using anti-VSV-G MAb P5D4 (Sigma, St. Louis, Mo.). The buoyant density of uncomplexed VSV-G is approximately 1.10–1.15. The formation of the lipid-DNA-VSV-G complex results in a shift of the buoyant density of some of the VSV-G to approximately 1.05, a position that corresponds to the lipofection maximum of the sample. Interestingly, the position of maximal transfection efficiency of the VSV-G liposome was several fractions heavier than the lipofectin-DNA complex itself, a result consistent with the presence of added VSV-G protein in the VSV-G liposome.

Example 2

Transfection Employing Polybrene (A) A DNA-liposome complex was prepared according to the manufacturer's directions by adding 2.5 μg of lipofectin to 50 μl of DMEM. Lipofectin was obtained from GIBCO BRL/Life Technologies (Grand Island, N.Y.). Polybrene was obtained from Sigma (St. Louis, Mo.). After incubation for 30 min at room temperature, the lipofection complex was mixed with 0.5 μg of plasmid DNA (pCMV-luc expressing the firefly luciferase gene from the immediate early promoter-enhancer of the human cytomegalovirus) in 50 μl DMEM, and incubated for 15 min at room temperature. The resulting DNA-lipofectin complex was added to the cells and replaced with fresh DMEM containing 10% FBS after 12 hours incubation. BHK and 208F cells (X. Li et al., Virology (1989) 171:331–41) were lipofected with the complex. Luciferase activity was measured as described by Li et al., and expressed as relative light units/μg protein in cell lysates. Cells were grown in Dulbecco's modified Eagle medium (DMEM) containing 10% (vol/vol) fetal bovine serum (FBS) in a 10% $CO_2$ atmosphere at 37° C. All lipofections were performed with cells grown to approximately 80% confluency in 12-well microtiter plates. Cells were washed twice with DMEM and fresh DMEM containing varying concentrations of FBS with or without added polybrene (8 μg/ml).

Figure 2A:
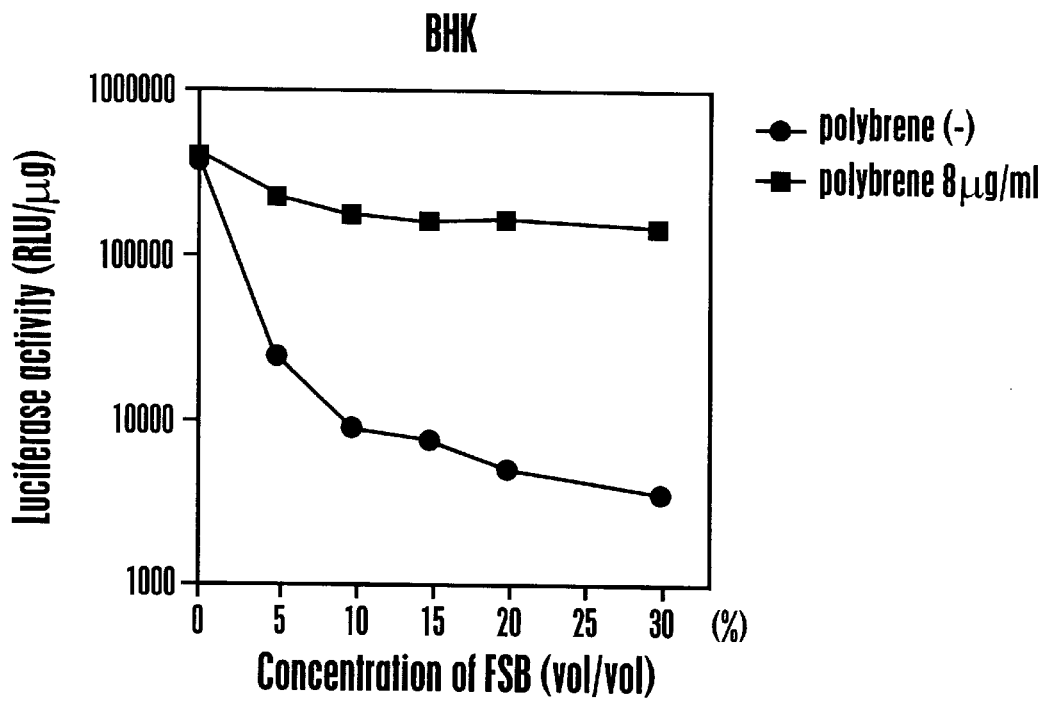
FIG. 2 shows the results of transfecting BHK cells (FIG. 2A) or 208F cells (FIG. 2B) with or without polybrene, in the presence of varying amounts of serum.
Figure 2B:
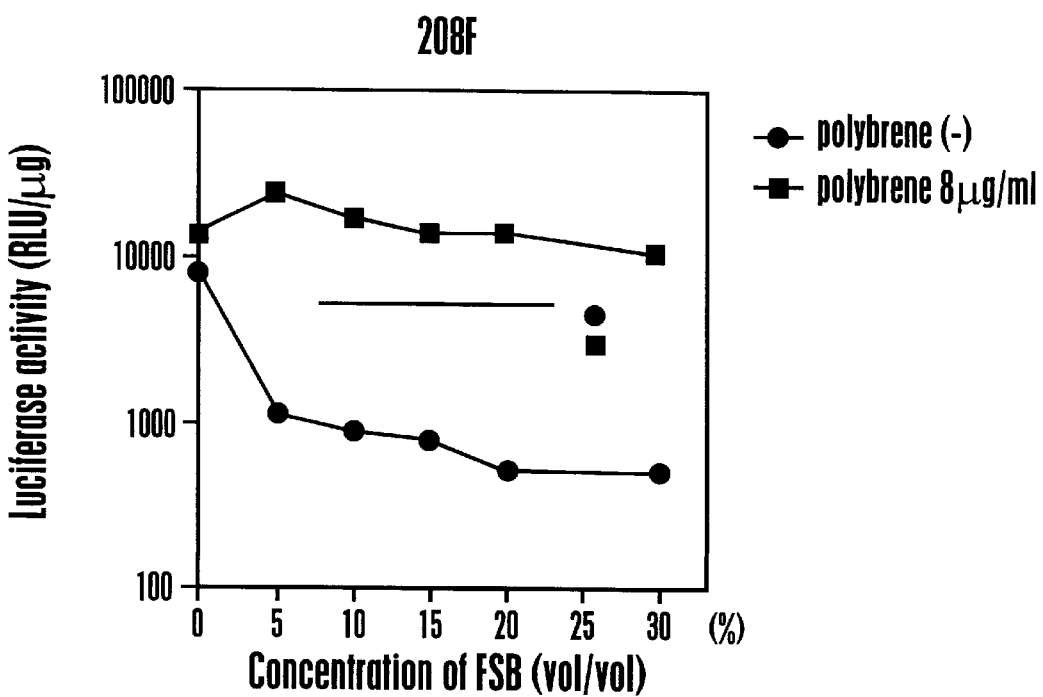

Results were obtained by measuring the luminescence generated from each lipofected cell line. Each concentration was run in triplicate, and reported as the mean±SD. The results, shown in FIG. 2, demonstrate that transfection efficiency is much lower in the presence of serum unless polybrene is added to the culture medium prior to lipofection.

Figure 3A:
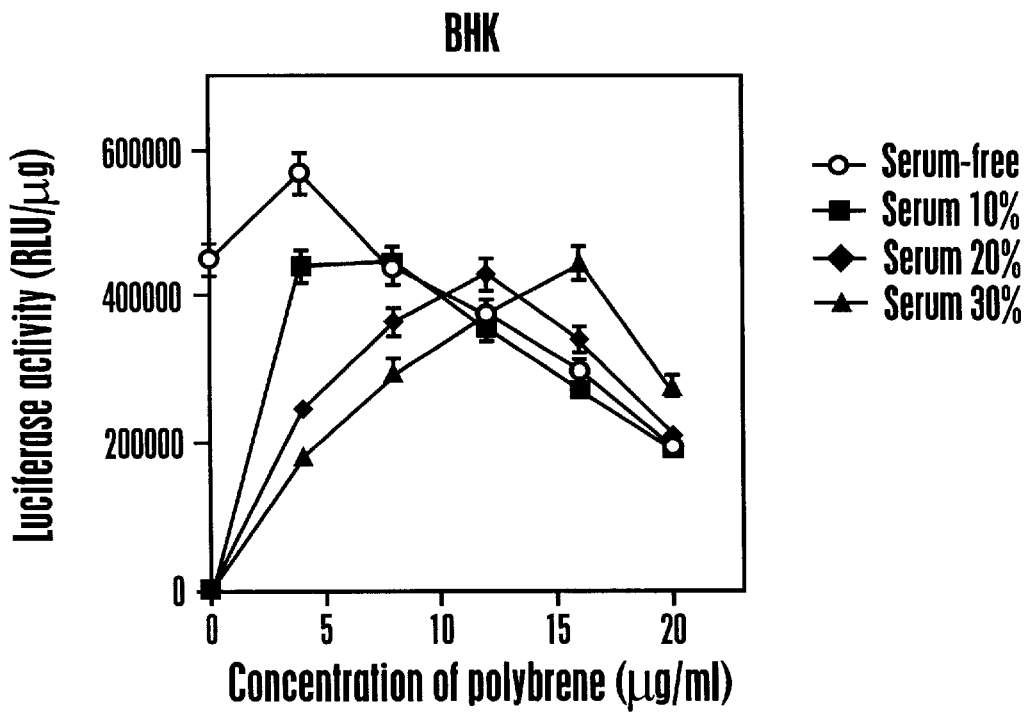
FIG. 3 shows the results of transfecting BHK cells (FIG. 3A) or 208F cells (FIG. 3B) with varying amounts of polybrene, in the presence of varying amounts of serum.
Figure 3B:
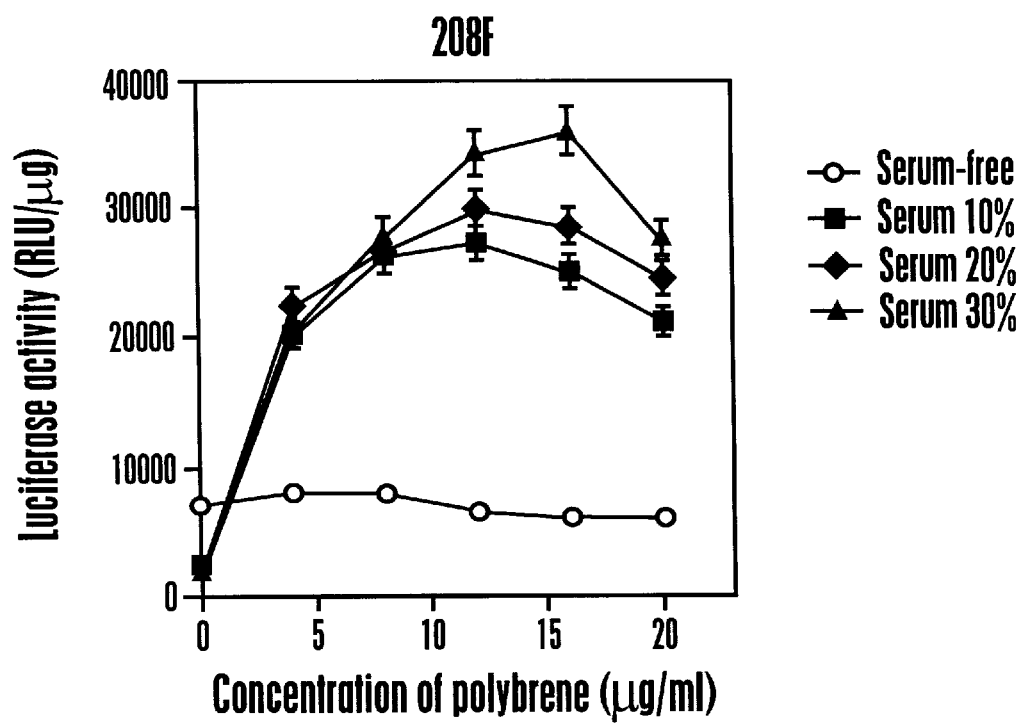

(B) The effects of various concentrations of polybrene were compared in the presence or absence of serum at a concentration of 10%, 20% or 30%. Polybrene was added to culture medium at concentrations of 0, 5, 10, 15, or 20 μg/ml, just before lipofection. The results, shown in FIG. 3, demonstrate that addition of 5–20 μg/ml polybrene just prior to lipofection increases the efficiency of transfection in the presence of serum.

Figure 4:
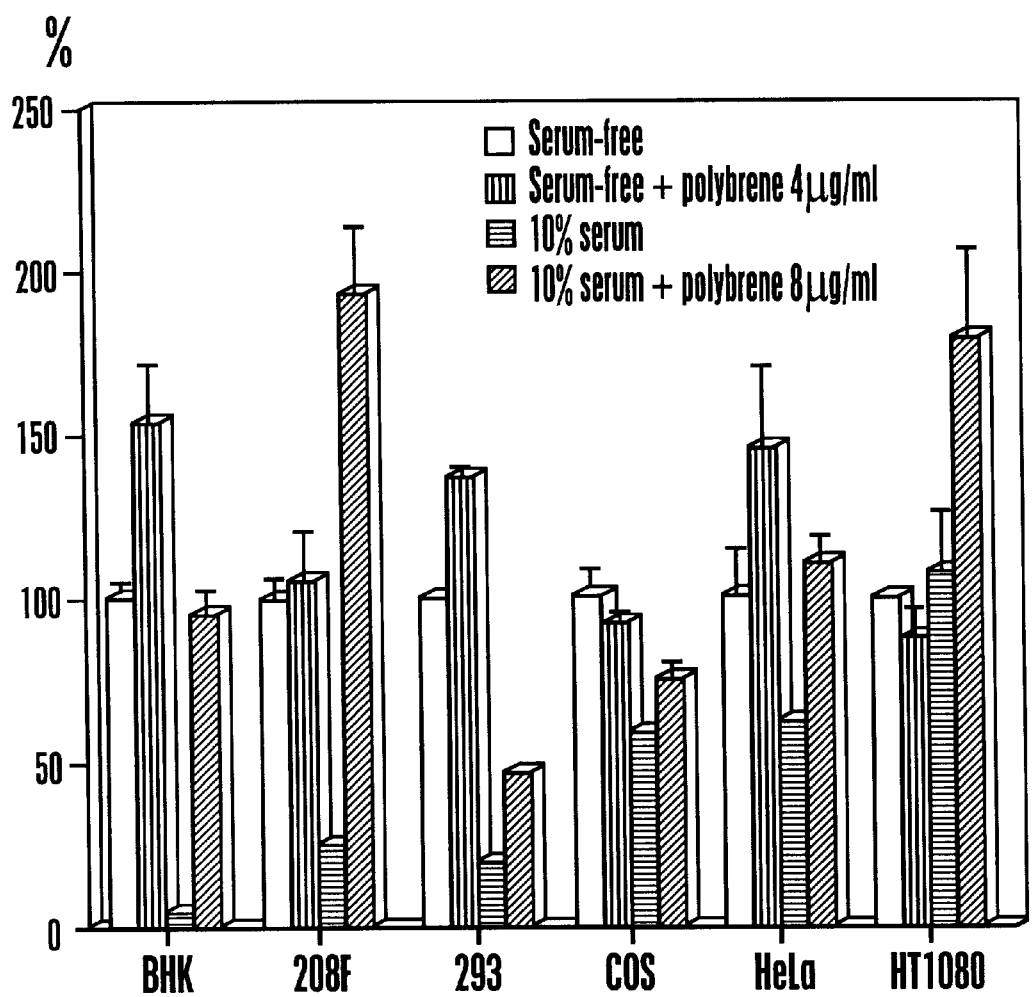
FIG. 4 shows the results of transfecting a variety of cells in the presence or absence of serum and the presence or absence of polybrene.

(C) The procedure of part (A) above was repeated, substituting COS, HeLa, 293 and HT1080 cells for the BHK and 208F cells. Results were normalized, assuming 100% for lipofection in the absence of serum. The results, shown in FIG. 4, show that transfection was less efficient in the presence of serum, but more efficient in the presence of polybrene. In some cases, transfection was more efficient in the presence of serum and polybrene together than in the absence of serum.

What is claimed is:

1. A method for introducing nucleic acids into a host cell in the presence of serum, said method comprising contacting said host cell with a nucleic acid-lipid complex and a transfection aid composition comprising between 300–400 ng of VSV-G to each 2.5 µg of nucleic acid-lipid complex.

2. The method of claim 1, wherein the nucleic acid-lipid complex comprises a complex of DNA and lipofectin.

3. The method of claim 1, wherein said VSV-G is fusogenically active.

4. The method of claim 1, further comprising contacting the host cell with a polycation transfection aid composition.

5. The method of claim 2, wherein the medium containing said host cell is contacted with said nucleic acid-lipid complex within 30 minutes of being contacted with said transfection aid.

6. The method of claim 3, wherein said medium is contacted with said nucleic acid-lipid complex within 10 minutes of being contacted with said transfection aid.

7. A method for preparing VSV-G for use as a transfection aid, said method comprising:

providing a producing cell comprising an expression vector encoding VSV-G operable in said producing cell;

culturing said producing cell in medium under conditions which result in expression of VSV-G to provide a conditioned medium;

purifying VSV-G from said conditioned medium by centrifugation under non-denaturing conditions to provide fusogenically active VSV-G.

8. The method of claim 4, wherein the polycation transfection aid composition consists of polybrene.

9. The method of claim 8, wherein the polybrene is present at a concentration in the polycation transfection aid composition of between 5 and 20 µg/ml.

10. The method of claim 9, wherein the host cell is contacted with the polybrene transfection composition immediately before the cell is contacted with the nucleic acid-lipid complex.

11. A composition for effecting lipid-mediated transfection in the presence of serum, said composition comprising a transfection-effective lipid; 300–400 ng of VSV-G and polybrene.

12. The composition of claim 11, wherein the polybrene is present at a concentration in the composition of between 5 and 20 µg/ml.

13. A method for introducing nucleic acids into a host cell in the presence of serum, said method comprising contacting said host cell with a nucleic acid-lipid complex and a transfection aid composition comprising 300–400 ng VSV-G to each 2.5 µg of nucleic acid-lipid complex.

* * * * *